US006541518B2

United States Patent
Shanbrom

(12) United States Patent
(10) Patent No.: US 6,541,518 B2
(45) Date of Patent: Apr. 1, 2003

(54) ENHANCED PRODUCTION OF SAFE PLASMA PREPARATIONS

(75) Inventor: Edward Shanbrom, Santa Ana, CA (US)

(73) Assignee: Shanbrom Technologies, LLC, Ojai, CA (US)

( * ) Notice: Subject to any disclaimer, the term of this patent is extended or adjusted under 35 U.S.C. 154(b) by 0 days.

(21) Appl. No.: 09/778,681

(22) Filed: Feb. 7, 2001

(65) Prior Publication Data

US 2003/0022149 A1 Jan. 30, 2003

Related U.S. Application Data

(63) Continuation-in-part of application No. 09/694,178, filed on Oct. 23, 2000.

(51) Int. Cl.⁷ .............................................. A61K 31/19
(52) U.S. Cl. ...................................................... 514/557
(58) Field of Search ........................... 424/667; 514/557

(56) References Cited

U.S. PATENT DOCUMENTS

| | | | | |
|---|---|---|---|---|
| 3,803,115 | A | * 4/1974 | Fekete et al. | 260/112 B |
| 4,086,218 | A | * 4/1978 | Shanbrom | 260/112 B |
| 4,305,871 | A | * 12/1981 | Shanbrom | 260/112 B |
| 4,327,086 | A | * 4/1982 | Fukushima et al. | 424/117 |
| 4,925,665 | A | * 5/1990 | Murphy | 424/532 |
| 4,977,246 | A | * 12/1990 | Lee et al. | 530/383 |
| 5,196,428 | A | * 3/1993 | Meanwell | 514/253 |
| 6,037,116 | A1 | * 3/2002 | Wiggins et al. | 435/1.1 |

FOREIGN PATENT DOCUMENTS

| | | | | |
|---|---|---|---|---|
| BE | 6326435 | * | 2/1962 | |
| EP | 188008 | * | 7/1986 | |
| EP | 0 272 551 | | 6/1998 | A61L/2/18 |
| RU | 2033611 | * | 4/1995 | |
| WO | 93/04678 | | 3/1993 | A61K/31/395 |
| WO | 93/21933 | | 11/1993 | A61K/33/18 |
| WO | 96/18292 | | 6/1996 | A01N/1/02 |

OTHER PUBLICATIONS

J. L. Veron, et al., *Combined Cohn/chromatography purification process for the manufacturing of high purity human albumin from plasma*, 1993, pp. 183–188.

K. Pedersen, *Inhibition of bacterial haemolysis on blood ager medium by oxalate or citrate used as anticoagulants*, 1973, p. 384.

D. Thompson, et al., *Fibrin Glue: A review of its preparation, efficacy, and adverse effects as a tropical hemostat*, 1988, pp. 946–952.

S. Arrighi, et al., *Process for the isolation of highly purified factors IX, X and II from prothrombin complex or human plasma*, 1995, pp. 183–188.

\* cited by examiner

*Primary Examiner*—Alton Pryor
(74) *Attorney, Agent, or Firm*—Crosby, Heafey, Roach & May, LLC

(57) ABSTRACT

Derivatives of simple carboxylic acids, particularly trisodium citrate and other citrate salts are effective agents for enhancing the production of blood clotting factors. Addition of citrate to plasma, especially at concentrations between 2 and 10% by weight, does not appreciably denature labile proteins. However, citrate is effective in inactivating or inhibiting a variety of pathogenic microorganisms. Further, the added citrate potentiates or enhances the killing of microorganisms by heat treatment. The added citrate causes a dramatic increase in the weight of cryoprecipitate that can be produced from plasma by the usual procedures. The majority of significant clotting factors are greatly concentrated in the resulting cryoprecipitate. Increasing the amount of citrate in blood bags so that the final concentration will be at least 2% by weight results in plasma that provides improved platelet concentrates because added citrate helps eliminate contaminating microorganisms.

13 Claims, 1 Drawing Sheet

ENHANCED PRODUCTION OF SAFE PLASMA PREPARATIONS

The present application is a continuation in part of U.S. patent application Ser. No. 09/694,178, filed on Oct. 23, 2000 and incorporated by reference herein.

BACKGROUND OF THE INVENTION

1. Area of the Art

The present invention relates to an improved method for producing increased amounts of safe coagulation factor concentrates from blood plasma

2. Description of the Prior Art

There are a number of medical indications for administration of "clotting" or "coagulation" factors from human blood. These factors are proteins that cause the clotting of blood to staunch bleeding from wounds, etc. Individuals with any of a series of genetic abnormalities affecting the proteins responsible for blood coagulation are afflicted with a disease (hemophilia) in which the blood fails to clot normally, subjecting the individual to the danger of uncontrolled bleeding. For many years this condition has been treated by administering concentrates of the missing or defective proteins. Many clotting factors are synthesized in the liver so that victims of liver disease are also in need of augmentation of their clotting factors. Additionally, there are other important medical uses for clotting-related factors.

While some of the clotting factors are currently produced through biotechnology, at this time there is still no cost effective method of artificially manufacturing all of these proteins. Further, the "artificially produced" factors tend to be more expensive. Many of the "minor" factors are not yet (and may never be) available from biotechnology sources and so must be purified from donated human blood. This is especially true in Third World countries where the biotechnology products are generally not affordable. Therefore, much of the supply of antihemophilia factor (AHF, also known as Factor VIII), and other blood clotting factors are prepared from pooled human plasma. A hemophiliac requires treatment for a whole lifetime. Victims of liver disease and other users of clotting factors may also require prolonged treatment. Therefore, these patients are exposed to blood products produced from the blood of a large number of donors.

The presence of AIDS (Acquired Immuno Deficiency Syndrome) virus or HIV in the blood supply means that hemophiliacs and other users of clotting factors have become infected with this terrible disease. Although tests to screen out AIDS-tainted blood have been improved, some infected blood does slip by. Even if the AIDS problem is solved, the danger of other blood-borne diseases, such as the various types of hepatitis and other, as yet unknown, infectious agents, makes it desirable to reduce or eliminate virus and other disease organisms from plasma used to prepare clotting factors. One way of achieving this goal is to reduce the use of pooled plasma products since "one bad apple spoils the entire barrel". However, even with the use of clotting factors derived from a single donor, there is still danger. Even though tests may show the donor is free of known disease, the donor may be incubating a disease that will later show on the tests or the donor may harbor a yet unknown disease or a yet unknown strain of a known disease. These dangers have been lessened by use of plasma pre-treatments that inactivate disease organisms. Unfortunately, the available treatments either do not inactivate all types of disease organisms or damage the labile clotting factors during the process of inactivating disease organisms.

The basic methods for preparing clotting factor concentrates from blood have not changed greatly over the last few decades. Generally, a concentrate of clotting factors is derived from pooled plasma by a cryoprecipitation step. Various additives such as ethanol or polyethylene glycol are usually added to enhance the efficiency of the cryoprecipitation step. Following cryoprecipitation, the partially purified factors may be further purified by additional precipitation steps or by chromatographic methods, and most recently by methods utilizing monoclonal antibodies. For additional information on the basic techniques of clotting factor purification and the history of the development of these methods, the reader is directed to U.S. Pat. Nos. 3,560,475. 3,631,018, 3,682,881, 4,069,216, and 4,305,871 and 5,770,704 by the present inventor, the contents of which are incorporated herein by reference, and the references cited therein.

SUMMARY OF THE INVENTION

It is an object of the present invention to provide enhanced yields of cryoprecipitate;

It is a further object of the present invention to inactivate and/or enhance the inactivation of disease organisms within plasma at the same time that cryoprecipitate production is enhanced.

Derivatives of simple carboxylic acids, particularly trisodium citrate and other citrate salts (hereinafter "citrate") are shown to be unexpectedly effective agents for enhancing the production of blood clotting factors. It is believed that other small carboxylic acids may show similar properties. Isocitric acid, in particular, appears to show these properties. To date most of the tests have been made with citric acid and its salts. Addition of citrate to plasma, especially at concentrations between 2 and 10% by weight, does not appreciably denature labile proteins. However, in this concentration range citrate is effective in inactivating or inhibiting a variety of pathogenic microorganisms. Further, the added citrate potentiates or enhances the killing of microorganisms by heat treatment. That is, heating of the material to relatively low temperatures (i.e., above 45° C.) which do not denature proteins enhances the killing of microorganisms in the presence of citrate. Significantly, added citrate causes a dramatic increase in the weight of cryoprecipitate that can be produced from plasma by the usual procedures. The majority of significant clotting factors are greatly concentrated in the resulting cryoprecipitate. The supernatant contains little if any of these clotting factors. It is apparent that increasing the amount of citrate in blood bags so that the final concentration will be at least 2% by weight results in plasma that can be used to produce improved platelet concentrates and enhanced cryoprecipitate. The added citrate can help eliminate or suppress contaminating microorganisms and can itself be removed by ion exchange or similar methods well known in the art.

DETAILED DESCRIPTION OF THE INVENTION

Figure 1:
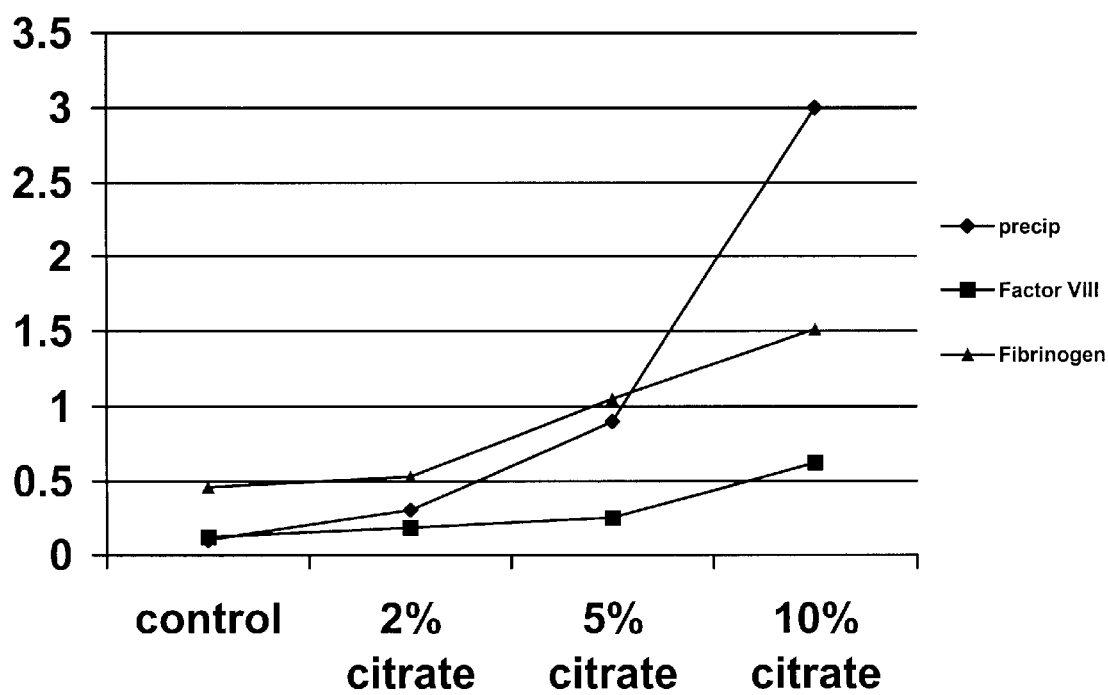
FIG. 1 is a graphic representation of the improvement in cryoprecipitate yield resulting from the present invention.

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide enhanced production of plasma proteins along with inactivation of blood borne disease organisms.

The traditional method for producing clotting factors, as well as many of the presently used methods, operate because many plasma proteins responsible for clotting precipitate (i.e., form cryoprecipitate) from solution at low temperatures when they are sufficiently concentrated. When a protein solution is frozen, ice crystals form and proteins, which are excluded from the crystals become increasingly concentrated. Cooling or freezing the water lowers the chemical activity of the water. Depending on the particular proteins, the proteins may actually fall out of solution, i.e., form a precipitate, if the protein more readily interacts with itself or with other proteins than with water. When the chemical activity of water is lowered such precipitation is favored. This process may denature the proteins (make them irreversibly insoluble), so it is usual to freeze protein solutions rapidly and to a low temperature (i.e., $-20°$ C. or lower) to minimize the formation of ice crystals and to prevent the growth of those crystals that do form. This is done to limit protein denaturation on ice crystal surfaces. However, even when freezing is carried out with great care, ice crystals may cause "activation" of the prothrombin complex, resulting in spontaneous clot formation.

The first step in the typical procedure for producing plasma cryoprecipitate is to centrifuge whole blood to separate the plasma from the red blood cells. This procedure is well known in the art and is often accomplished in special centrifuges that hold individual blood bags so that the plasma/red cell separation occurs without even opening the blood bag. Following the centrifugation it is common practice to express the supernatant plasma into a "satellite" blood bag for further processing. Once the plasma is separated, the typical procedure is to rapidly freeze the plasma and to then slowly thaw the frozen plasma at $4°$ C., during which thawing the clotting factors and other proteins form a cryoprecipitate which can be readily harvested by filtration or centrifugation. This cryoprecipitate is not rendered irreversibly insoluble and can be readily redissolved in a low ionic strength buffer, as is well known in the art.

Cryoprecipitation results when the removal of water from the immediate vicinity of the protein molecules causes the protein molecules to preferentially associate with each other rather than with water. This "removal" of water may represent changes in the solubility of the proteins with changes in temperature (i.e., water becomes less effective at dissolving the proteins). The process may also be accomplished or enhanced through the use of additives which "tie up" the water and cause it to interact less with the proteins. These additive substances can be any of a number of hydrophilic materials such as ethanol, polyethylene glycol, heparin, Pluronic RTM polyol polymers and various "salts" such as ammonium sulfate or ammonium acetate. The "salting out" of proteins from solution is a classical biochemical procedure. These and other materials used to increase the yield of cryoprecipitate generally operate to decrease the effective activity of water in the mixture. That is, the water molecules preferentially interact with the added hydrophilic material instead of with the proteins. This permits the proteins to interact with each other and, therefore, precipitate from solution. Similarly, lowering the temperature also decreases the activity of water, allowing protein-protein interactions to predominate.

The hydrophilic additives just mentioned have the advantage of being relatively inexpensive and easy to use. However, their use usually necessitates additional washing steps to ensure that the additives are not carried over into the final product. Some additives may also damage or denature the labile clotting factors one is seeking to purify. The present inventor has discovered that one of the agents frequently used as an anticoagulant in blood fractionation unexpectedly serves to enhance cryoprecipitate formation. Citrate (trisodium citrate or similar salts as well as derivatives of other low molecular weight carboxylic acids such as isocitric acid) has unusually favorable properties when used in blood fractionation procedures at levels significantly higher than those traditionally used as an anticoagulant. Citrate is a fairly effective chelator of calcium ions. By effectively lowering the calcium ion level, citrate inhibits a considerable variety of blood clotting pathways all of which depend on the presence of calcium ions. However, citrate has generally not been employed as an agent to enhance the preparation of cryoprecipitate proteins from plasma and other blood fractions.

The following table shows the enhanced production of cryoprecipitate caused by increasing the level of trisodium citrate in plasma. As the citrate is increased, the weight of recovered cryoprecipitate is increase. When the cryoprecipitate is redissolved in a fixed quantity of water, the increasing amount of cryoprecipitate yields increasing amounts of Factor VIII and fibrinogen as compared to the original plasma. The precise reason for this phenomenon is not known. However, it seems reasonable to speculate that one action of citrate may be to inhibit the activation of clotting factors. Since many of these factors act as proteases when activated, activation naturally "chews up" and reduces the yield of many proteins. However, lack of inactivation does not seem sufficient to account for the entire increase in cryoprecipitate yield.

| Treatment | Cryoprecipitate | Factor VIII | Fibrinogen |
| --- | --- | --- | --- |
| control | 0.1 g | 120% | 46 mg/dl |
| 2% citrate | 0.3 g | 180% | 53 mg/dl |
| 5% citrate | 0.9 g | 247% | 105 mg/dl |
| 10% citrate | 3.0 g | 622% | 152 mg/dl |

These data are graphically represented in FIG. 1. These results indicate that as the citrate concentration is increased the amount of recovered clotting factors increases fairly linearly. However, at the highest concentration of citrate it would appear that there may be an increase in the precipitation of other proteins. It may be possible to adjust the citrate concentration to favor the precipitation of different proteins.

On the surface one might not expect citrate to be more effective than any hydrophilic salt. In terms of salting proteins out of solution one would expect various agents to operate based on their colligative properties. That is, one might expect equimolar concentrations of various agents to behave similarly. This does not appear to be the case with citrate and cryoprecipitate formation.

The following quantities of either salt (NaCl) or citrate (trisodium citrate) were added to 40 ml aliquots of fresh human plasma. After thorough mixing the samples were frozen overnight at $-70°$ C. and then completely thawed at $4°$ C. The samples were then centrifuged at 4000 RPM for 20 min to harvest the cryoprecipitate. An attempt was made to match the effective sodium concentration between the sodium chloride and sodium citrate on the basis that each molecule of trisodium citrate would provide three sodium ions whereas each molecule of sodium chloride would provide only a single sodium ion. This attempt at compensation was inaccurate because the matching should be done on a molar rather than a percent basis. However, this failed experiment points out the incredible superiority of sodium citrate over sodium chloride for producing cryoprecipitate. In the following table the citrate (trisodium citrate) or salt (sodium chloride) are shown first as weight percentages and then as molarities. The third column shows the effective osmotic effect of the solutions, which is two times higher on a molar basis for citrate than for sodium chloride. This is because each molecule of sodium chloride releases only two particles (one sodium ion and one chloride ion) whereas each molecule of trisodium citrate releases four particles (three sodium ions and one citrate ion). Because the molecular weight of trisodium citrate is almost 5 times greater than that of salt to get equal osmotic effects one must use about 2.5× (on a weight basis) as much trisodium citrate as sodium chloride. That is, for an accurate matching more citrate rather than more salt should have been used.

| Weight % | Molarity | Osmotic Effect | Cryoprecipitate |
| --- | --- | --- | --- |
| Control | — | — | 0.18 g |
| 2% citrate | 0.07 | 0.28 | 0.52 g |
| 5% citrate | 0.17 | 0.68 | 1.3 g |
| 10% citrate | 0.34 | 1.36 | 3.6 g |
| 6% sodium chloride | 1.02 | 2.04 | 0.12 g |
| 15% sodium chloride | 2.56 | 5.13 | 0.14 g |
| 30% sodium chloride | 5.13 | 10.26 | 0.15 g |

These results show that the effect of citrate on cryoprecipitate production is not strongly related to the colligative or osmotic properties of the citrate. Sodium chloride seems to prevent cryoprecipitate formation. Only at osmotic levels that are greatly above those of the maximal citrate concentration, cryoprecipitate formation begins to approach that of the control plasma.

Following the experiment the supernatants and the original plasma (control) were sent to a clinical chemistry laboratory to determine the presence of various blood proteins including clotting factors. These results are shown in the following table.

| Weight % | Fibrinogen (mg/dl) | Factor VIII (%) | Albumin (g/dl) |
| --- | --- | --- | --- |
| Control | 287 | 24 | 3.2 |
| 2% citrate | 216 | 6 | 3.1 |
| 5% citrate | 114 | <3 | 3.2 g |
| 10% citrate | <40 | <3 | 3.2 g |
| 6% NaCl | 298 | 30 | 3.1 g |
| 15% NaCl | 229 | 24 | 3.0 g |
| 30% NaCl | 97 | 9 | 2.9 g |

As the amount of citrate is increased the levels of fibrinogen and Factor VIII in the supernatant decrease dramatically. At the same time the level of albumin (the major plasma protein) is essentially unaffected. In other words, most of the clotting factors precipitate and are found in the cryoprecipitate, but little or no albumin precipitates. In the case of sodium chloride equimolar concentrations are much less effective at precipitating the clotting factors. One has to go up to 30% sodium chloride to see a significant precipitation of the clotting factors. However, at this level the albumin also begins to precipitate. Citrate is far more effective at selectively precipitating the clotting factors.

Although citrate appears to strongly influence the precipitation of the clotting factors, it does not appear to denature the proteins. Citrate at 2% by weight was added to an aliquot of plasma which was stored at room temperature for six days. Clotting factors and platelets were counted at the beginning and the end of the time period. As compared to control plasma, the addition of citrate did not appear to harm the clotting factors. There is actually some suggestion that the citrate may actually help preserve platelets.

| Measurement | Day 1 | Day 6 |
| --- | --- | --- |
| 2% Citrate Plasma | | |
| Fibrinogen (mg/dl) | 243 | 239 |
| Factor II (%) | 104 | 91 |
| Factor V | 49 | 22 |
| Factor VII (%) | 81 | 72 |
| Factor VIII (%) | 103 | 92 |
| Factor IX (%) | 106 | 95 |
| Factor X (%) | 92 | 97 |
| Platelets ($10^3/10^{-6}$L) | 311 | 239 |
| PT (sec) | 14.1 | 16.2 |
| PTT (sec) | 31.4 | 47.9 |
| Control Plasma | | |
| Fibrinogen (mg/dl) | 241 | 239 |
| Factor II (%) | 103 | 93 |
| Factor V | 58 | 25 |
| Factor VII (%) | 86 | 69 |
| Factor VIII (%) | 100 | 89 |
| Factor IX (%) | 106 | 92 |
| Factor X (%) | 93 | 85 |
| Platelets ($\times 10^3/10^{-6}$L) | 317 | 192 |
| PT (sec) | 13.7 | 19.5 |
| PTT (sec) | 32.5 | 50.2 |

Significantly, bacteriology experiments showed that 2% trisodium citrate strongly inhibits growth of *scherichia coli* and completely inhibits the growth of *Staphylococcus epidermidis*. Growth of bacteria (primarily skin bacteria from inadequate surface disinfection) in platelet concentrates significantly lowers the useable life of platelet-rich solutions. Addition of citrate inhibits bacterial growth thereby potentially extending the life of such concentrates. As has been demonstrated above, addition of citrate does not damage the plasma constituents and actually significantly enhances the production of cryoprecipitate. Therefore, it is proposed to significantly increase the level of citrate in blood collection bags from the 0.4% currently used for anticoagulation to at least 2% trisodium citrate by weight. This level would inhibit or kill contaminating microorganisms and would render the plasma more suitable for production of cryoprecipitate. It is a simple matter to add additional trisodium citrate just before cryoprecipitate production where levels beyond 2% are needed.

Added citrate appears to enhance the susceptibility of microorganisms to a variety of "disinfecting agents" including heat. In one experiment 2% sodium citrate was added to a typical bacterial growth broth. Twenty five ml aliquots of the broth was spiked with $1\times10^4$ organisms of either *Escherichia coli* or *Staphylococcus epidermidis*. Samples of the broth were brought to 2% by weight trisodium citrate and then subjected to "pasteurization" at 65° C. for either 5 or 10 min. after which the samples were plated on growth media and incubated. As shown in the following tables, the 10 min treatment caused total destruction of the bacteria. However, the 5 min treatment without citrate did not kill all of the bacteria. Addition of citrate enhances the ability of heat to kill microorganisms. Further, added citrate appears to stabilize the proteins against heat denaturation.

A problem with platelet concentrates and with plasma is the growth over time of bacteria that are originally present in very low numbers. Some of the contaminating bacteria apparently come from the skin surface when the blood is obtained by venipuncture. Further, there is growing evidence that blood is not completely aseptic. That is, there are normally a small number of bacteria circulating in the human bloodstream. Normal immunity prevents the overgrowth of these bacteria. To simulate this situation 10 ml samples of human plasma were inoculated at very low levels (10 organisms per ml) with the bacteria listed in the following table. Either normal plasma or plasma with 2% by weight of citrate was employed. The samples were incubated at room temperature for seven days with a sample plated on growth agar at each time point. Three different human plasmas were run, but all produced identical results. In the table "ng"="no growth" while "+" indicates some bacterial growth and "++" indicates more extensive growth. The symbol "N" indicates normal plasma while "C" indicates plasma containing 2% by weight citrate.

|  | Day 1 | | Day 2 | | Day 3 | | Day 4 | | Day 5 | | Day 6 | | Day 7 | |
|---|---|---|---|---|---|---|---|---|---|---|---|---|---|---|
| Inoculum | N | C | N | C | N | C | N | C | N | C | N | C | N | C |
| a) | ng | ng | ng | ng | ng | ng | ng | ng | ng | ng | + | ng | ++ | ng |
| b) | ng | ng | ng | ng | ng | ng | ng | ng | ng | ng | + | ng | ++ | ng |
| d) | ng | ng | ng | ng | ng | ng | ng | ng | ng | ng | + | ng | ++ | ng |
| e) | ng | ng | ng | ng | ng | ng | ng | ng | ng | ng | + | ng | + | ng |
| f) | ng | ng | ng | ng | ng | ng | ng | ng | ng | ng | + | ng | + | ng |
| g) | ng | ng | ng | ng | ng | ng | ng | ng | ng | ng | ng | ng | ng | ng | a) *Escherichia coli*
b) *Klebsiella pneumoniae*
c) *Staphylococcus epidermidis*
d) *Staphylococcus aureus*
e) *Pseudomonas fluorescens*
f) *Yersinia enterocolitica*
g) *Serratia marcescens*

At day six and seven the normal plasma showed growth of all of the inoculated bacteria species except for Serratia. On the otherhand, none of the plasma samples containing citrate demonstrated any bacterial growth. This indicates that 2% by weight citrate is able to strongly inhibit the growth of a wide range of bacteria. Combining these results with the favorable platelet results demonstrates that addition of 2% or more citrate to platelet concentrates can preserve the concentrates against bacterial growth without damaging the platelets. If there is any concern about excess citrate in the platelets, it can be readily removed by treatment with an anion exchange resin or similar material.

It was suspected that the failure to observe Serratia was due to the slow growth rate of this organism. Therefore, the experiment was repeated using *Serratia marcescens* and *Staphylococcus epidermidis* to inoculate plasma samples at the level of 100 organisms per ml. In this case the one day time point for Serratia showed 92 colonies while that for Staphylococcus showed 101 colonies for the normal plasma. No growth was observed in either case for the citrate-containing plasma.

The precise mechanism by which citrate and similar molecules act is not know. Multiple carboxyl groups appear important particularly in the case of cryoprecipitate. Oxalic and lactic acids are less effective. It seems possible that there is some type of charge interaction that favors the precipitation of the clotting factors. While chelating ability is clearly important for the well known anti-coagulation effects of citrate, chelation may not be central to the present invention as isocitrate is believed to be a poorer chelating agent than citrate. It may also be that the participation of many of the effective molecules in the tricarboxylic acid cycle may also be related to their effects—particularly those on bacterial growth.

The following claims are thus to be understood to include what is specifically illustrated and described above, what can be obviously substituted and also what incorporates the essential idea of the invention. The illustrated embodiment has been set forth only for the purposes of example and that should not be taken as limiting the invention. Therefore, it is to be understood that, within the scope of the appended claims, the invention may be practiced other than as specifically described herein.

I claim:

1. A method for preventing pathogens in plasma and for enhancing the production of cryoprecipitate from plasma comprising the steps of adding at least 2% by weight of a low molecular weight carboxylic acid selected from the group consisting of isocitric acid, citric acid and salts thereof to the plasma to make treated plasma, freezing the treated plasma and thawing the frozen treated plasma to form a cryoprecipitate and a supernatant wherein less than 10% of Factor VIII in the plasma is left in the supernatant.

2. The method of claim 1, wherein the low molecular weight carboxylic acid is citric acid.

3. The method of claim 2, wherein a trisodium salt of the citric acid is added to the plasma.

4. The method of claim 1, wherein the plasma is a platelet concentrate.

5. The method of claim 1 further comprising a step of heating the treated plasma above 45° C., wherein a pasteurization enhancer and protein stabilizer consists essentially of the low molecular weight carboxylic acid.

6. The method of claim 1 further comprising a step of removing the carboxylic acid or the carboxylic acid salt by means of ion exchange chromatography.

7. The method of claim 1, wherein the plasma is collected into a blood bag containing the carboxylic acid or the carboxylic acid salt.

8. A method for preventing pathogens in plasma and for enhancing the production of cryoprecipitate from plasma comprising the steps of adding at least 2% by weight of citric acid or a salt citric acid to the plasma to make treated plasma, freezing the treated plasma and thawing the frozen treated plasma to form a cryoprecipitate and a supernatant wherein less than 10% of Factor VIII in the plasma is left in the supernatant.

9. The method of claim 8, wherein the plasma is collected into a blood bag containing the citric acid or the citric acid salt.

10. The method of claim 8, wherein a trisodium salt of the citric acid is added to the plasma.

11. The method of claim 8, wherein the plasma is a platelet concentrate.

12. The method of claim 8 further comprising a step of removing the citric acid or the citric acid salt by means of ion exchange chromatography.

13. The method of claim 8 further comprising a step of heating the treated plasma above 45° C., wherein a pasteurization enhancer and protein stabilizer consists essentially of the citric acid or the citric acid salt.

* * * * *